US00PP37372P2

(12) United States Plant Patent
O'Connell

(10) Patent No.: US PP37,372 P2
(45) Date of Patent: Apr. 14, 2026

(54) ***CRASSULA* PLANT NAMED 'Halo'**

(50) Latin Name: *Crassula platyphylla*
Varietal Denomination: Halo

(71) Applicant: Altman Specialty Plants llc, Vista, CA (US)

(72) Inventor: Renee O'Connell, Pala, CA (US)

(73) Assignee: Altman Specialty Plants llc, Vista, CA (US)

( * ) Notice: Subject to any disclaimer, the term of this patent is extended or adjusted under 35 U.S.C. 154(b) by 0 days.

(21) Appl. No.: 19/264,362

(22) Filed: Jul. 9, 2025

(51) Int. Cl.
*A01H 6/32* (2018.01)
*A01H 5/12* (2018.01)

(52) U.S. Cl.
USPC ..... Plt./373
CPC ..... *A01H 6/32* (2018.05); *A01H 5/12* (2013.01)

(58) Field of Classification Search
USPC ..... Plt./373
CPC ..... A01H 6/32; A01H 5/02
See application file for complete search history.

*Primary Examiner* — Keith O. Robinson

(57) ABSTRACT

A new and distinct cultivar of *Crassula* plant named 'Halo' is disclosed, characterized by gracefully arching branches of delicate green, margined in creamy yellow splashes. In addition, the new cultivar 'Halo' branches and offsets heavily, enhancing production in the commercial nursery. The new cultivar is a *Crassula*, part of the Crassulaceae complex that includes *Crassula, Crassula, Pachyphytum, Graptopetalum, Sedum* and others. *Crassula* is a popular genus, typically produced as container plants or as landscape plants.

1 Drawing Sheet

Latin name of the genus and species: *Crassula platyphylla.*

Cultivar denomination: 'HALO'.

BACKGROUND OF THE INVENTION

The new cultivar, *Crassula* 'Halo', is the result of a naturally-occurring branch mutation of the unnamed *Crassula platyphylla*. The new cultivar, *Crassula* 'Halo' was discovered by the inventor in March of 2022 in a commercial greenhouse in Vista, California.

Asexual reproduction of the new cultivar 'Halo' was first performed in Vista, California, at a commercial greenhouse, by vegetative cuttings in May 2022. 'Halo' has since produced multiple generations and has shown that the unique features of this cultivar are stable and reproduced true to type.

SUMMARY OF THE INVENTION

The cultivar 'HALO' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'HALO'. These characteristics in combination distinguish 'HALO' as a new and distinct *Crassula* cultivar:

1. The new cultivar *Crassula platyphylla* 'Halo' forms heavily offsetting variegated plants.
2. *Crassula platyphylla* 'Halo' exhibits gracefully arching branches of delicate green, margined in creamy yellow splashes.

3. The attractive clustering of *Crassula platyphylla* 'Halo' is particularly suited to use in patio mixed plantings as the variegated leaves enhance the other colors.
4. *Crassula platyphylla* 'Halo' branches heavily as a young plant, resulting in enhancement of propagation in a commercial nursery environment and a fuller product at an earlier age.

Plants of the new cultivar 'HALO' are similar to plants of the parent in most horticultural characteristics, however, plants of the new cultivar 'HALO' differ in the following;

1. *Crassula platyphylla* 'Halo' is a variegate, whereas the parent variety, *Crassula platyphylla* is not.
2. *Crassula platyphylla* exhibits leaves that blush reddish in strong light, whereas *Crassula platyphylla* 'Halo' displays somewhat elongated green leaves with marginal splashes of creamy yellow.
3. *Crassula platyphylla* 'Halo' displays a larger, more graceful morphology than does *Crassula platyphylla.*

COMMERCIAL COMPARISONS

Plants of the new cultivar 'HALO' are comparable to the commercial cultivar *Crassula platyphylla* 'Daydream', U.S. Plant Pat. No. 33,928. The two *Crassula* cultivars are similar in most horticultural characteristics; however, the new cultivar 'HALO' differs in the following:

1. *Crassula platyphylla* 'Halo' produces olive green leaves, margined with creamy yellow splashes, whereas *Crassula platyphylla* 'Daydream' U.S. Plant Pat. No. 33,928 produces leaves with more slender apple green midstripes, margined with white and blushed in rose under certain conditions.
2. *Crassula platyphylla* 'Halo' displays a somewhat more lax morphology than does *Crassula platyphylla* 'Daydream'.

Plants of the new cultivar 'HALO' can also be comparable to the unpatented, unnamed cultivar of *Crassula platyphylla* found in the horticultural market. The two *Crassula* cultivars are similar in most horticultural characteristics; however, the new cultivar 'HALO' differs in the following:

1. *Crassula platyphylla* 'Halo' is a variegated plant, whereas *Crassula platyphylla* is not.
2. *Crassula platyphylla* exhibits green leaves, blushing red in full sun, whereas *Crassula platyphylla* 'Halo' displays somewhat olive leaves, margined in creamy white splashes.
3. *Crassula platyphylla* is a bit more compact growing than *Crassula platyphylla* 'Halo', which produces a more flowing morphology.

BRIEF DESCRIPTION OF THE PHOTOGRAPH

The photograph was taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of the new cultivar *Crassula* 'Halo'. The accompanying figure illustrates in full color a plant of *Crassula* 'Halo', at about 9 months, grown at a nursery (approximately 2500 foot candles) in Vista, California in an 8-inch pot.

DETAILED BOTANICAL DESCRIPTION

In the following description, color references are made to The Royal Horticultural Society Colour Chart, 2015 edition, except where general terms of ordinary dictionary significance are used. The following observations and measurements describe 'Halo' plants grown in a commercial nursery in Vista, California. Temperatures ranged from about 34° F. to 90° F. No artificial light, photoperiodic treatments or chemical treatments were given to the plants. Natural light conditions were approximately 2500 to 3000 fc of light. Measurements and numerical values represent averages of typical plant types.

Botanical classification: *Crassula platyphylla* 'HALO'.

PROPAGATION

Type of propagation typically used: Terminal vegetative cuttings.

Time to initiate roots: About 16 days at approximately 25° C.

Root description: Fibrous.

PLANT

Age of plant described: Approximately 9 months.

Container size of the plant described: 1 gallon pot.

Growth habit: Multi-branched shrublet.

Height: Approximately 12 cm.

Plant spread: Approximately 28 cm.

Branching characteristics: Abundant sub-opposite lateral branches. About 4 breaks from a pinch on average.

*Length*.—Main branches about 5 cm to 6 cm, lateral branches about 5 cm to 12 cm.

*Width*.—7 mm.

*Color*.—Lowermost colored RHS Greyed-Green 195B. Uppermost Green 138C.

*Texture*.—Glabrous.

*Strength*.—Moderately strong. Not brittle or easily broken.

*Internode*.—About 1 cm.

FOLIAGE

Leaf:

*Arrangement*.—Opposite decussate.

*Average length*.—Approximately 3.5 to 4.5 cm.

*Widest width*.—Approximately 2.6 cm.

*Depth*.—3 mm.

*Shape of blade*.—Oblanceolate.

*Apex*.—Acute.

*Base*.—Attenuate.

*Margin*.—Entire.

*Texture of top surface*.—Glabrous. Very slightly glaucous.

*Texture of bottom surface*.—Glabrous. Very slightly glaucous.

*Quantity of leaves per plant*.—Average 16 per branch.

*Leaf internode*.—1 cm.

*Color*.—Young foliage upper side: Center RHS Green 138B, thick margins Yellow-Green 150D. Young foliage, under side: Center RHS Green 138B, thick margins Yellow-Green 150D. Mature foliage upper side: Center RHS Green 138B, thick margins Yellow 4C. Mature foliage upper side: Center RHS Green 138B, thick margins Yellow 4C.

Venation: Indistinguishable from leaf blade.

FLOWER

Flowering not observed to date.

REPRODUCTIVE ORGANS

Unknown, flower has not yet been observed.

OTHER CHARACTERISTICS

Fruits and seeds: Unknown; has not flowered to date.

Temperature tolerance: Tolerates temperatures from approximately 2° C. to 39° C.

Disease/pest resistance: No increased nor decreased resistance to normal diseases and pests of *Crassula* has been observed.

Drought tolerance: Tolerates at least 3 weeks of high temperatures without supplemental water, showing no serious damage to plant.

What is claimed is:

1. A new and distinct cultivar of *Crassula* plant named 'HALO' as herein illustrated and described.

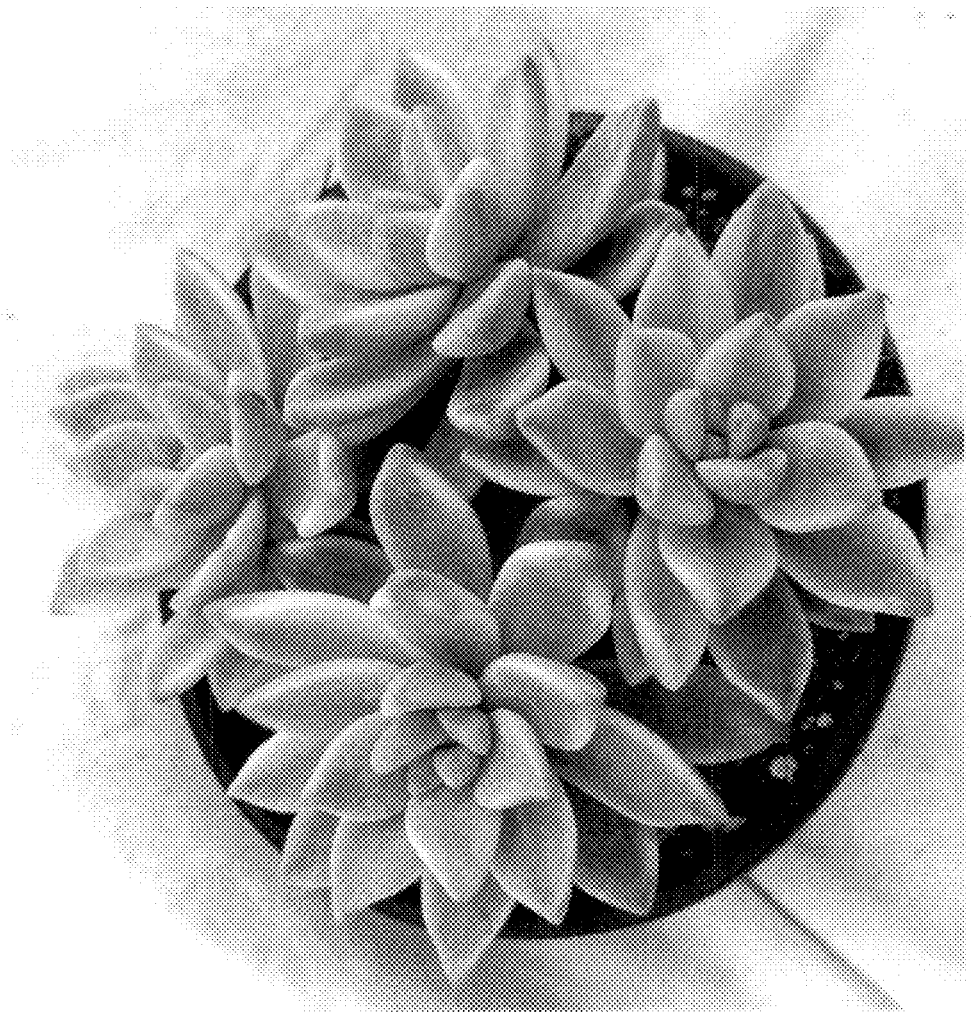

* * * * *